Figure 1:
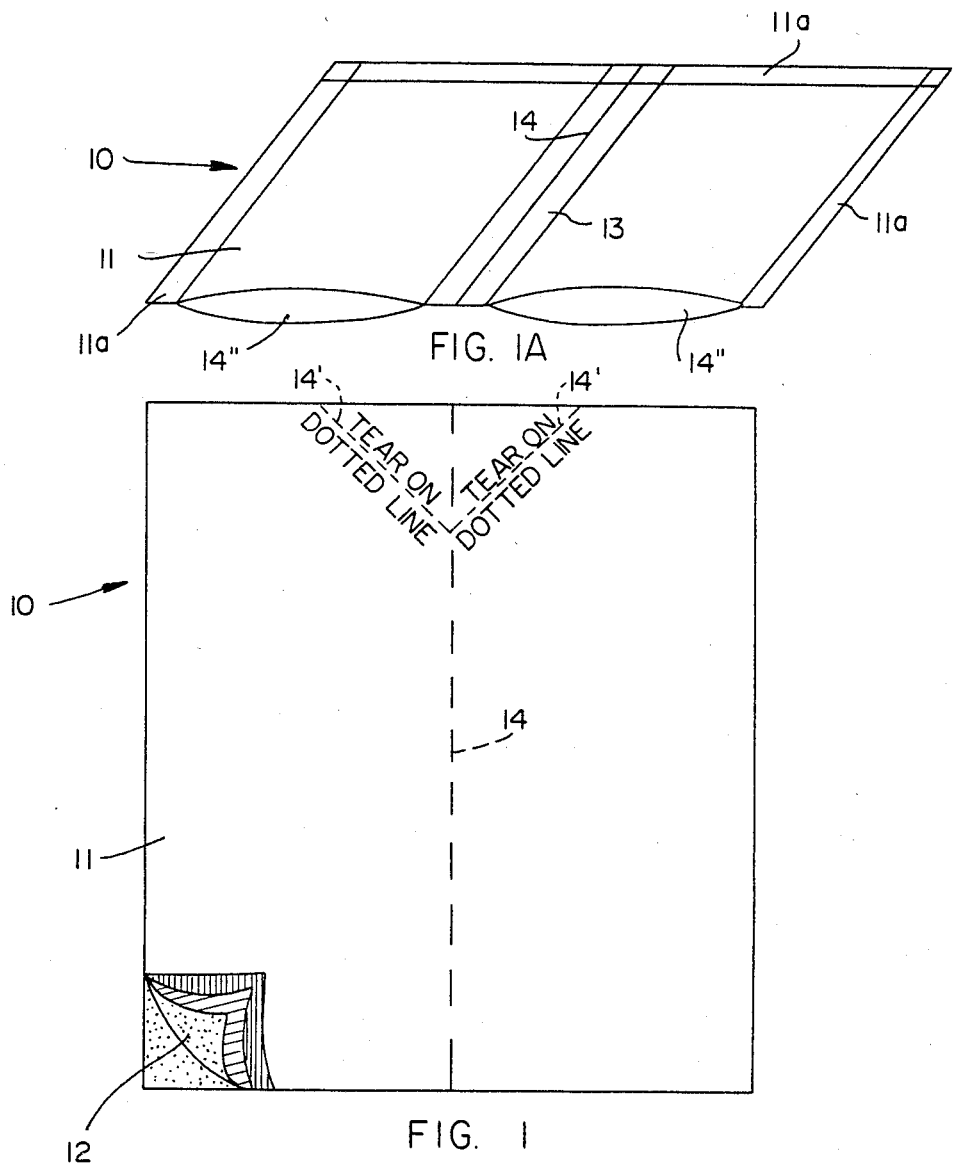

United States Patent [19]

Simon et al.

[11] Patent Number: 4,592,487

[45] Date of Patent: * Jun. 3, 1986

[54] DENTIFRICES

[76] Inventors: Gilbert I. Simon, 1111 Midland Ave., Bronxville, N.Y. 10708; Roy T. Witkin, 23 Broadview Rd., Westport, Conn. 06880

[*] Notice: The portion of the term of this patent subsequent to Jun. 4, 2002 has been disclaimed.

[21] Appl. No.: 752,236

[22] Filed: Jul. 3, 1985

[51] Int. Cl.$^4$ .................. A61K 7/20; A61K 33/18; A61K 31/79

[52] U.S. Cl. ........................ 222/94; 424/51; 424/53

[58] Field of Search ............... 424/51, 53; 222/94

[56] References Cited

U.S. PATENT DOCUMENTS

| | | | |
|---|---|---|---|
| 1,535,529 | 4/1925 | Hopkins | 424/53 |
| 1,566,218 | 12/1925 | Leland | 424/49 |
| 2,789,731 | 4/1957 | Marraffino | 222/94 |
| 3,175,731 | 3/1965 | Ellman | 222/94 |
| 3,874,558 | 4/1975 | Rockefeller | 222/92 |
| 4,060,179 | 11/1977 | McGhie | 222/92 |
| 4,098,435 | 7/1978 | Weyn | 222/94 |
| 4,211,341 | 7/1980 | Weyn | 222/94 |
| 4,330,531 | 5/1982 | Alliger | 424/53 |
| 4,487,757 | 12/1984 | Kiozpeoplou | 424/7.1 |
| 4,521,403 | 6/1985 | Simon et al. | 424/51 |
| 4,528,180 | 7/1985 | Schaeffer | 424/52 |

OTHER PUBLICATIONS

Dannenberg et al., Amer. J. Hosp. Pharmacy 35: 528, May 1978, Betadine Hydrogen Peroxide Irrigation Solution Incompatibility.

*Primary Examiner*—Shep K. Rose
*Attorney, Agent, or Firm*—Jacobs & Jacobs

[57] ABSTRACT

Dentifrices comprising two components each of which comprises ingredients usually present in toothpastes or toothpowders, one component containing an iodophor as a source of derived iodine and the other component containing a source of active or nascent oxygen. The two components are kept out of contact with one another and separately filled into a suitable package so arranged and constructed that the components can be admixed and dispensed together to form an antimicrobial, antiplaque non-toxic dentifrice ready for use.

16 Claims, 5 Drawing Figures

DENTIFRICES

The present invention relates to dentifrices and more particularly to toothpastes having antimicrobial and antiplaque properties and especially to a two-component antimicrobial antiplaque toothpaste of which one component, prior to the combining of which with the other component contains, in addition to the usual or conventional dentifrice ingredients, a predetermined amount of an iodophor, such as the povidone-iodine complex (PVP-I) and the other component, in addition to the same or usual or conventional ingredients, contains an equal amount of a source of active or nascent oxygen such as carbamide peroxide. During use after combining and admixing the two components the dentifrice provides an unusually effective antimicrobial antiplaque nontoxic non-staining amount of iodine derived from the iodophor, the antimicrobial activity of which is enhanced or potentiated by interaction with the source of oxygen and/or the active or nascent oxygen therefrom together with good cleaning, polishing and debriding action. The iodophor and the oxygen source components are kept apart physically to avoid premature interaction or loss of efficacy before the toothpaste is used. This is accomplished by means of any known or suitable packaging and dispensing means or by a specially designed container/mixer/dispenser device.

Formulations for conventional dentifrices and toothpastes are well known and readily available and usually contain phosphates as cleaning and polishing agents, finely divided carbonates or silica as mild abrasive and cleaning agents together with sorbitol as a humectant and a thickening agent such as carboxymethylcellulose for obtaining and maintaining the desired thickness consistency. Conventional dentifrices and toothpastes usually also contain flavoring and/or sweetening ingredients in a small amount to impart a pleasing or palatable taste thereto and the dentifrices further contain a substantial amount of water with which the other ingredients are thoroughly admixed. The presence of a flavoring and/or sweetening agent in the dentifrices of this invention is particularly advantageous to neutralize or overcome any possible unpalatability or unpleasant taste due to the iodine content. The amount of water used may be adjusted depending on the particular dentifrice being formulated and the thickness or consistency desired and furthermore many of the present day dentifrices also contain a fluoride such as stannous fluoride, sodium fluoride or sodium monofluorophosphate as an anticaries agent as may our novel dentifrices.

It has been found that however useful and effective conventional dentifrices may be for cleaning and debriding purposes, they do not usually have adequate activity against microbes and the plaque which results from the gradual build-up of microorganisms on the enamel and adjacent surfaces of the dental structure of the teeth. As a result the dentifrices must be used more frequently or the abrasives contained therein must have a greater abrasive or cleansing power which involves the risk of scratching or otherwise damaging the tooth enamel which in turn reduces resistance to the formation of plaque and cavities.

Many dentifrices are known and commercially available which are basically similar in composition but may vary in the amount and nature of ingredients, particularly in connection with the use of abrasives such as calcium carbonate, silica or alumina or phosphates such as dicalcium or tricalcium phosphates and their particle sizes. Most of the usual commercial dentifrices are opaque, commonly white, from the nature of the ingredients or from the optional addition of a small amount of titanium dioxide or other whitening or brightening agent and still other commercial dentifrices are of the transparent or translucent gel type containing cleaning and polishing agents in one or more of the gel layers or parts.

Some of these toothpaste formulations are illustrated in "A Formulary of Detergents and Other Cleaning Agents" compiled by Michael and Irene Ash, Chemical Publishing Co., N.Y., 1980; e.g.:

| Formula 1 | |
|---|---|
| Ingredients | Percentages |
| Water | 25.30 |
| CMC (12 HP) | 1.25 |
| Sorbitol Solution (USP) | 23.75 |
| Dicalcium Phosphate Dihydrate | 48.00 |
| Preservatives | q.s. |
| Flavor, sweetener | q.s. |

PROCEDURE

In preparing the above toothpaste formulation, the water is heated to about 80° to 85° C., the carboxymethylcellulose is gradually added with until complete hydration occurs, the stirring is continued and the sorbitol and preservatives are added and blended in until uniform, following which the dicalcium phosphate dihydrate is slowly added and the materials are then mixed under slow agitation until a smooth paste is obtained which is then cooled to 40° to 45° C. and deaerated under vacuum. Any additional or supplemental components are then added under slow agitation followed by blending to uniform consistency and then filling into the toothpaste tube or container.

| Formula 2 | |
|---|---|
| Ingredients | Percentages |
| Sodium Carboxymethylcellulose (med. visc.) | 0.70 |
| Water | 23.40 |
| Saccharin | 0.15 |
| Water | 2.00 |
| Sorbitol (70% solution) | 12.50 |
| Glycerin | 12.50 |
| Dicalcium Phosphate Dihydrate | 45.00 |
| Flavor | 1.00 |
| Sodium Lauryl Sulfate | 1.50 |
| Preservative | q.s. |

PROCEDURE

The above toothpaste formula is prepared in substantially the same way as the toothpaste in Formula 1, except that no heating is carried out, by mixing and blending operations to obtain a smooth desired consistency and avoiding incorporation of air.

| Formula 3 | |
|---|---|
| Ingredients | Percentages |
| Sodium Carboxymethylcellulose (med. visc.) | 0.80 |
| Water | 28.05 |
| Saccharin | 0.15 |
| Water | 2.00 |

-continued

Formula 3

| Ingredients | Percentages |
| --- | --- |
| Sorbitol (70% solution) | 15.00 |
| Glycerin | 10.00 |
| Dicalcium Phosphate Dihydrate | 30.00 |
| Tricalcium Phosphate | 10.00 |
| Flavor | 1.00 |
| Sodium Lauryl Sulfate | 1.50 |
| Preservative | q.s. |

PROCEDURE

The composition of Formula 3 is prepared in the same or substantially the same manner as Formula 2 using slow mixing under mild agitation and avoiding incorporation of air.

Formula 4

| Ingredients | Percentage |
| --- | --- |
| Lathanol LAL-70 Powder | 3.0 |
| Tricalcium Phosphate | 26.6 |
| Gum Tragacanth | 1.0 |
| Glycerin | 44.5 |
| Saccharin | 0.2 |
| Water | 23.1 |
| Flavor | 0.6 |

PROCEDURE

The toothpaste of the foregoing formula is low foam and prepared by dispersing the gum in 25 parts of the glycerin, dissolving the saccharin in water and slowly adding the same to a mixture of the gum tragacanth and glycerin followed by continuous agitation until the product is smooth. The balance of the glycerin is combined with the tricalcium phosphate and the Lathanol LAL-70 to form a thick paste which is then thoroughly admixed until uniform, whereupon the flavor is incorporated. In this formulation the tricalcium phosphate may be increased or decreased to obtain the desired consistency.

Any of these or similar dentifrice formulas can be adapted to the present invention by dividing it into the two components and adding the PVP-I to one component and the peroxide to the other component and then filling packages or pouches with the separate parts for subsequent discharge as an admixture ready for use.

While available dentifrices such as toothpastes of varying composition and consistency are generally satisfactory, they ordinarily lack any component or ingredient which is particularly directed to provide or retard antiplaque formation and the destruction or inhibition of microorganisms normally existing on the gums and teeth in the oral cavity. The present invention is thus particularly directed to dentifrices such as toothpastes and toothpowders which are provided, in addition to the usual components as above set forth, with a predetermined amount of an iodophor such as the povidone-iodine complex or Biopal, which iodophor has been found, due to the iodine derived therefrom during use, to be particularly effective with respect to antimicrobial and antiplaque activity and this activity is enhanced or potentiated by interaction therewith or thereon of active or nascent oxygen released from a peroxy compound. Various suitable sources of active or nascent oxygen may be employed preferably such as $H_2O_2$, carbamide peroxide, benzoyl peroxide or other oxygen releasing agent or by sodium chlorite as a source of $ClO_2$.

Since the iodophor and the source of oxygen when admixed have the capability of prematurely interacting, it is necessary to form the dentifrice in two separate component parts, of which one component contains the iodophor and the other component contains the source of oxygen as well as the other dentifrice ingredients and this can be readily accomplished by, for example, using a toothpaste tube having a partition therein to form two compartments so that upon discharging the contents of the compartments from the mouth of the toothpaste tube they intermix and interact to give the enhanced or potentiated antimicrobial and antiplaque dentifrice formulation. Since the admixed components are only on the toothbrush bristles or teeth for a short period of time, they have sufficient duration of action to bring about the desired effects when the dentifrice is used for brushing teeth.

It has been found that the amount of iodophor need only be relatively small in proportion to the entire composition of the dentifrice and since PVP-I, although freely water soluble, is commercially available in the form of a water-soluble brownish powder, about 6%± of such powder is incorporated in the one component of the dentifrice formulation. The source of oxygen need only be about 2%± by weight of the other component of the toothpaste formulation although these proportions may vary as we are not limited to the use of these particular percentages.

As explained above, PVP-I and the source of oxygen from a peroxy compound tend to interact with one another virtually immediately upon contact and consequently the dentifrice formulations are made up as two-component separate subsequently combined compositions, one of which contains the PVP-I and the other of which contains the peroxy compound. In a variant form of the two-component dentifrice container structure the PVP-I formulation and the peroxy formulation are segregated in separate compartments of a partitioned or subdivided package or container and admixed and discharged together. A tubular structure or device may furthermore be used such as that of U.S. Pat. No. 3,175,731 or British Specification No. 962,757 published July 1, 1964, the contents of which are hereby made a part hereof by reference for the toothpaste container or package, or tubes similar thereto may be used.

In the formulation of our novel toothpastes, the various individual components may differ not only as to their nature but as to their proportions, depending upon the desired physical properties of the final product. Some standard materials used in formulating toothpaste include, for example, 1% of a gelling agent, 10 to 30% of a humectant and 15 to 50% of an abrasive and polishing agent such as calcium carbonates or phosphates, together with a small amount, in the range of 0.1 to 0.2, of a sweetening agent such as saccharin and 1.0 to 1.5% of a flavoring agent such as spearmint, peppermint, menthol, ethanol, eugenol, wintergreen, anethole, anise, eucalyptus and cinnamon. The surface active agent amounts to about 1.0 to 2.0% and is preferably sodium lauryl sulfate. The preservatives used in conventional dentifrices are not required in the formulations of this invention due to the inherent preservative nature of the active ingredients. When the toothpaste is desired to have anticaries activity, 0.1 to 1.0% is incorporated therein such as sodium fluoride, stannous fluoride and sodium monofluorophosphate. A small amount of coloring matter is added where it is desired to impart a particular tint or hue in an amount sufficient to give the desired coloration. The balance, to make up 100%, is water. The formulations are divided into two parts or compositions, one of which contains the iodophor and the other of which contains the source of oxygen.

In the accompanying drawings

Figure 2:
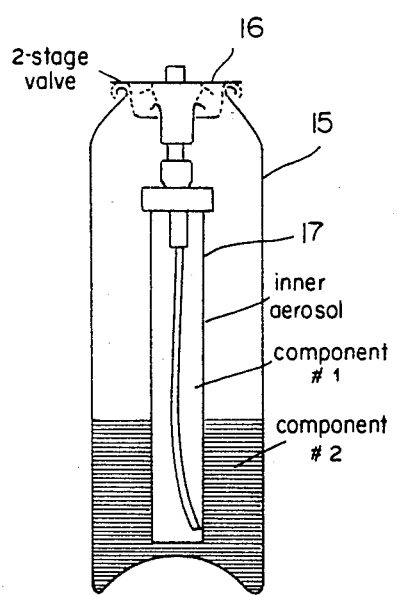
Figure 3:
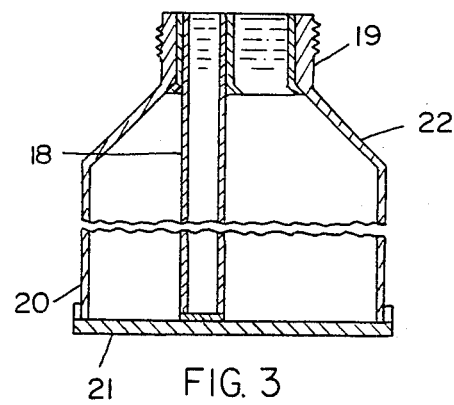
Figure 4:
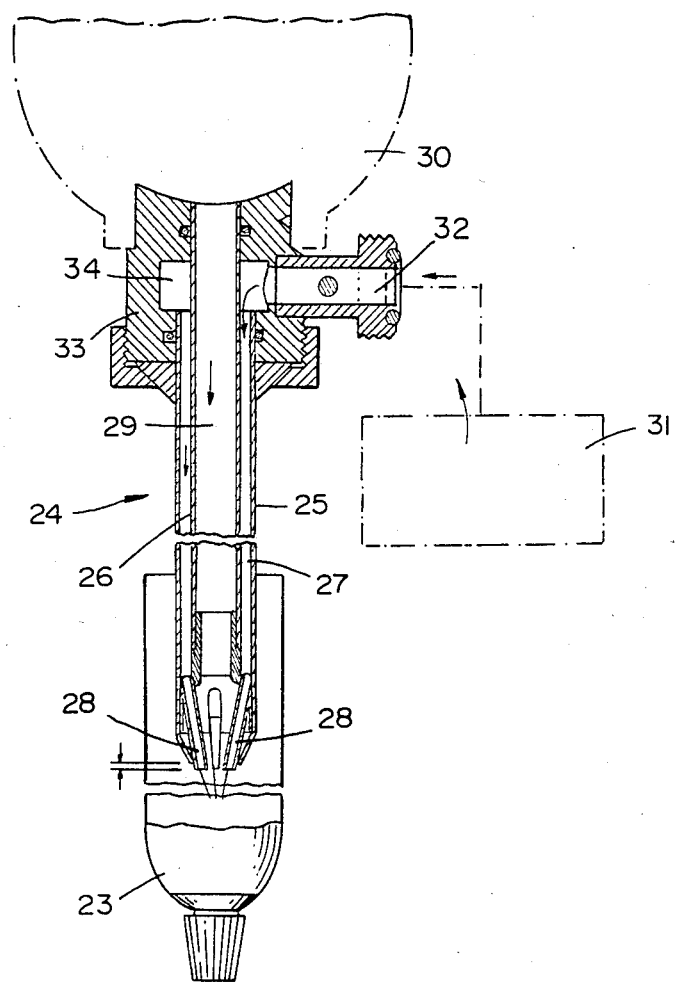

FIGS. 1 and 1A illustrate in plan and perspective views an embodiment of a two-compartment container or package for a dentifrice of the invention wherein the container or package is a heat sealed plastic lined aluminum pouch with a common tear-out section;

FIG. 2 diagrammatically illustrates a two-compartment valved aerosolized system for reception and discharge of our two-component dentifrice formulation;

FIG. 3 illustrates in vertical section a view of construction of toothpaste receptacle and dispenser according to U.S. Pat. No. 3,175,731 (FIG. 1 thereof), which can be used for a dentifrice according to this invention, and FIG. 4 is an elevational view partially in section of a structural arrangement according to British Specification No. 962,757 which can be used for filling a dentifrice tube with a dentifrice formulation according to our invention and for discharging the two components thereof from a common outlet or orifice.

Formulations of two-component or two-part dentifrices according to the present invention are illustrated by the following non-limitative examples:

EXAMPLE 1

Toothpaste

| Ingredients | PVP-I Component % by wgt. | Peroxide Component % by wgt. |
|---|---|---|
| Water | 26.64 | 31.39 |
| PVP-I (calculated as powder, 10% $I_2$) | 6.66 | — |
| Carbamide Peroxide | — | 1.86 |
| Sodium carboxymethylcellulose | 1.25 | 1.25 |
| Sorbitol | 23.75 | 23.75 |
| Dicalcium phosphate dihydrate | 40.2 | 40.2 |
| Sodium lauryl sulfate | 1.5 | 1.5 |
| Flavor, sweetener | q.s. | q.s. |
| Actives | 0.67% $I_2$ | 0.67% $H_2O_2$ |

Upon combining the components, the mixture provides
Actives { 0.34% $I_2$
            0.34% $H_2O_2$

EXAMPLE 2

Toothpaste

| Ingredients | PVP-I Component % by wgt. | Peroxide Component % by wgt. |
|---|---|---|
| PVP-I (calculated as powder, 10% $I_2$) | 10.0 | — |
| Carbamide Peroxide | — | 8.3 |
| Calcium carbonate | 34.0% | 40.0 |
| Sorbitol | 23.8 | 18.7 |
| Sodium lauryl sulfate | 1.5 | 1.5 |
| CMC (12 HP) | 1.3 | 1.3 |
| Water | 29.4 | 30.2 |
| Flavor, sweetener | q.s. | q.s. |

Actives in components: 1.0% $I_2$  3.0% $H_2O_2$
Actives in 1:1 mixture: 0.5% $I_2$/1.5% $H_2O_2$

EXAMPLE 3

Toothpaste

| Ingredients | PVP-I Component % by wgt. | Peroxide Component % by wgt. |
|---|---|---|
| PVP-I (calculated as powder, 10% $I_2$) | 10.0 | — |
|  | — | 8.3 |
| Silica (e.g., Syloid 244) | 15.0 | 20.0 |
| Sorbitol | 20.0 | 20.0 |
| Sodium lauryl sulfate | 1.5 | 1.5 |
| CMC (12 HP) | 3.0 | 3.0 |
| Water | 50.5 | 47.2 |
| Flavor, sweetener | q.s. | q.s. |

Actives in components: 1.0% $I_2$  3.0% $H_2O_2$
Actives in 1:1 mixture: 0.5% $I_2$/1.5% $H_2O_2$

EXAMPLE 4

Toothpowder

| Ingredients | PVP-I Component % by wgt. | Peroxide Component % by wgt. |
|---|---|---|
| PVP-I (calculated as powder, 10% $I_2$) | 10.0 | — |
| Dicalcium phosphate dihydrate | 69.0 | 70.7 |
| Calcium carbonate | 20.0 | 20.0 |
| Sodium lauryl sulfate | 1.0 | 1.0 |
| Flavor, sweetener | q.s. | q.s. |
| Carbamide peroxide | — | 8.3 |

To be packed in separate compartments of a powder dispensing container, which will dispense approximately equal portions of each component.

EXAMPLE 5

Toothpaste

| Ingredients | PVP-I Component % by wgt. | Peroxide Component % by wgt. |
|---|---|---|
| PVP-I (calculated as powder, 10% $I_2$) | 10.0 | — |
| Aluminum magnesium silicate (e.g. Veegum) | 1.5 | 1.5 |
| Benzoyl peroxide | — | 16.1 |
| Sodium carboxymethylcellulose (med. visc.) | 0.5 | 0.5 |
| Water | 30.3 | 24.2 |
| Sodium saccharine | 0.2 | 0.2 |
| Sorbitol (70% solution) | 15.0 | 15.0 |
| Glycerin | 10.0 | 10.0 |
| Dicalcium phosphate dihydrate | 26.0 | 26.0 |
| Tricalcium phosphate | 5.0 | 5.0 |
| Sodium lauryl sulfate | 1.5 | 1.5 |
| Flavor | q.s. | q.s. |

Actives in components: 1.0% $I_2$  3.0% $H_2O_2$
Actives in mixture: 0.5% $I_2$/1.5% $H_2O_2$

EXAMPLE 6

Toothpaste

| Ingredients | PVP-I Component % by wgt. | Peroxide Component % by wgt. |
|---|---|---|
| PVP-I (calculated as powder, 10% $I_2$) | 10.00 | — |
| Carbamide Peroxide | — | 8.3 |
| Sorbitol (70% solution) | 20.00 | 15.00 |
| Calcium pyrophosphate | 40.00 | 26.00 |
| Sodium monofluorophosphate | 0.76 | — |
| Glycerin | 5.00 | 10.00 |
| Sodium lauryl sulfate | 1.50 | 1.50 |
| Magnesium aluminum silicate | 0.40 | 1.50 |
| Sodium carboxymethylcellulose | 1.15 | 0.5 |
| Stannous gluconate (31% solution) | 10.00 | — |
| Water | 11.19 | 37.2 |
| Flavor | q.s. | q.s. |

EXAMPLE 7

Toothpaste

| Ingredients | % by wgt. PVP-I Component | % by wgt. Peroxide Component |
| --- | --- | --- |
| PVP-I (calculated as powder, 10% I$_2$) | 10.00 | — |
| Carbamide Peroxide | — | 8.30 |
| Sorbitol (70% solution) | 20.0 | 15.00 |
| Calcium pyrophosphate | 40.00 | 26.00 |
| Stannous fluoride | 0.40 | — |
| Glycerin | 5.00 | 10.0 |
| Sodium lauryl sulfate | 1.50 | 1.50 |
| Magnesium aluminum silicate | 0.40 | 1.50 |
| Sodium carboxymethylcellulose | 1.15 | 0.50 |
| Stannous gluconate (31% solution) | 10.00 | — |
| Water | 11.55 | 37.2 |
| Flavor | q.s. | q.s. |

EXAMPLE 8

Denture Cleaner

| Ingredients | % by wgt. PVP-I Component | % by wgt. Peroxide Component |
| --- | --- | --- |
| Veegum | 1.0 | 1.0 |
| Sodium carboxymethylcellulose (med. visc.) | 0.5 | 0.5 |
| Water | 28.9 | 28.9 |
| PVP-I (calculated as powder, 10% I$_2$) | 10.00 | — |
| Carbamide Peroxide | — | 8.3 |
| Saccharin | 0.1 | 0.1 |
| Sorbitol (70% solution) | 9.0 | 9.0 |
| Glycerin | 9.0 | 9.0 |
| Dicalcium phosphate (dihydrate) | 27.0 | 28.7 |
| Dicalcium phosphate (anhydrous) | 12.0 | 12.0 |
| Flavor | 0.5 | 0.5 |
| Sodium lauryl sulfate | 2.0 | 2.0 |

PROCEDURE

Dry blend the PVP-I (or carbamide peroxide), Veegum and the CMC and add to the water slowly, agitating continually until smooth. Add saccharin to the CMC and mix. Blend with the sorbitol and add the blend to the CMC and saccharin. Blend in the phosphates and add to the mixture, then add the flavor and the sodium lauryl sulfate, one at a time, to the other components and mix until uniform.

Package the two components in separate compartments of a two-component dispensing package, commonly available in the trade.

As will be apparent from the foregoing Examples, the antimicrobial actives in the two components can be varied as desired and the actives in a 1:1 mixture of the two components can be correspondingly varied to provide a composite toothpaste or toothpowder formulation containing the indicated amount of derived iodine and peroxide components. It will be understood also that the water content may vary depending upon the desired consistency or viscosity of the resulting toothpaste. Each of the ingredients of the Examples may further be varied in amount to produce a series of different toothpastes or toothpowders.

The cleaning or polishing ability of the formulations can also be varied either by changes in the amount and nature of the abrasive(s) such as dicalcium phosphate or calcium carbonate or silica or aluminum hydroxide gels may be optionally substituted in whole or in part. The amount of fluorine compound in the formulations is conventional and is in the amount of about 0.1% to 0.5% or up to 1% or more depending upon the particular fluorine compound used, sodium monofluorophosphate being preferred. It is to be considered as an optional inclusion in the above formulations where it is also desired to have an anticaries ingredient present, as some users seem to prefer non-fluoride toothpastes.

It is to be understood that the dentifrices of the invention are not dependent upon or limited to the use therewith of any specific container, pouch or other functionally utilizable package or filling means and that the drawings are intended as exemplary only and are not per se restrictive as to structure, filling arrangements or discharge orifices.

Referring to the drawings, FIGS. 1 and 1A show a two-compartment pouch 10 fabricated from aluminum 11 which is lined with an inert plastic material 12, the entire pouch being made of two rectangular or other suitably shaped upper and lower sheets or layers heat sealed at 11a around three edges of the periphery and also heat sealed for compartmenting purposes along the mid-line 13 which is optionally additionally provided with a series of space perforations or indentations 14 to facilitate bending or folding, the perforations being such as not to permit communication of the pouch compartments. The pouch is further provided with a common dotted tear line 14' so that the two parts or sections of the pouch may be bent or folded upon one another and the common pouch portion within the dotted (triangular) line 15 cut or torn out or removed, whereupon the pouch is ready for common discharge of the PVP-I and peroxide components, one of which is in each of the compartments of the pouch, each compartment being heat sealed at its open end 14" after being filled. When squeezing pressure is exerted on the pouch the two separate components are discharged in admixed form as a dentifrice formulation ready for use. The pouch compartments may be previously filled in any suitable or known manner, as for example by means of the devices disclosed elsewhere herein.

FIG. 2 shows a two compartment device into which the components of the examples can be individually filled and then discharged together under pressure, e.g. by means of aerosol or air pressure. The device comprises an outer generally cylindrically shaped container 15 of glass, metal or plastic having a two-stage valve 16 at its upper end connected with which is an inner cylindrically shaped downwardly extending tube or member 17 acting as a glass, metal or plastic inner aerosol connected to a 20 mm two-stage, one inch valve 16. The container 15 and the inner aerosol portion 17 operates as a two-compartment single shot unit via a 1" internal valve and when the two valves are operatively connected the inner aerosol operates as a single shot and empties its product into the outer container for discharging a single shot mixed product. The small innermost tube constitutes means for introducing a pressurized medium such as an aerosol or compressed air.

FIG. 3 is a section through a fluoride-containing dentifrice dispenser wherein the fluoride component or composition is disposed within the tubular member 18 which extends through an externally threaded closure cap-receiving hollow member 19 into which fits alongside tube 18 as shown a bottle-shaped container 20 which is secured or otherwise suitably fastened in a sealing base member 21. The container 20 may taper as shown at 22 and merge within externally threaded member 19 which is adapted for the reception of a conventional internally threaded screw cap (not illustrated). The use and operation of the dispenser is simple and is in accordance with the description in U.S. Pat. No. 3,175,731. FIG. 1 of which has been used as present FIG. 3 to illustrate an alternate form of dual container for containing two parts or components which can be discharged in admixed condition.

FIG. 4 shows a toothpaste tube 23 into which extends a double-walled annular member 24 having an outer casing 25 and an inner casing 26, thereby forming an annular space 27 leading to orifices 28 whereby material passing through the annular space and also through the inner tubular member 29 enables the toothpaste tube 23 to be filled with an admixture of two different compositions of which the main toothpaste supply is contained in chamber 30 and the secondary toothpaste supply is contained in the chamber 31 which is shown diagrammatically in dot-dash lines and from which the secondary toothpaste supply can be introduced into the pipe 32 mounted in the boss 33 provided with an annular compartment 34 which is in communication with the passageway in member 32. In this way, two different compositions such as the PVP-I component and the peroxide component, as exemplified in the foregoing examples and formulations, can be filled into a single tube which may be provided as hereinabove stated with a partition or division member (not illustrated) in order to keep the two parts or components physically out of contact with one another until they are to be admixed and discharged ready for use.

What is claimed is:

1. An antimicrobial antiplaque dentifrice comprising, in addition to conventional dentifrice ingredients in usual amounts, about 6%, calculated on the total weight of the dentifrice, of povidone-iodine complex or Biopal as iodophor as a first part and about 2%, on the same basis, of a separate source of active or oxygen such as carbamide peroxide as a second part, whereby during use of the dentifrice the two parts are admixed and provide an effective antimicrobial antiplaque non-toxic amount of iodine derived from the iodophor of the first part, the antimicrobial activity of which is enhanced or potentiated by interaction with the source of oxygen and/or the active or nascent oxygen released therefrom.

2. A dentifrice according to claim 1, wherein the oxygen source is $H_2O_2$, carbamide peroxide, benzoyl peroxide, sodium chlorite or other source of oxygen.

3. A dentifrice according to claim 1, wherein the oxygen source is carbamide peroxide and the peroxide formulation and the iodophor formulation are present in a 1:1 v/v proportion.

4. A dentifrice according to claim 1, wherein the iodophor is the povidone-iodine complex.

5. A dentifrice according to claim 1 formulated for use in paste, gel or powder form.

6. A non-toxic antiplaque, anticavity dentifrice in toothpaste or gel form containing as its active ingredients an antimicrobially active antiplaque amount of an iodophor formulation and carbamide peroxide formulation in approximately equal amounts, optionally including 0.1-1.0% by weight of the toothpaste or gel of an anticaries fluoride compound.

7. An antimicrobial, antiplaque dentifrice which during use is constituted of a mixture of two components, each of which components contains the same or similar conventional dentifrice components in like amounts but wherein one part contains an iodophor and the other part contains a compound which is a source of oxygen, the two components being kept separated from one another until they are to be used whereupon the components are admixed and dispensed as a complete dentifrice, the antimicrobial and antiplaque activity is enhanced or potentiated by interaction with the source of oxygen and/or the active or nascent oxygen released therefrom.

8. A dentifrice according to claim 7 in which each of the said components is filled into a separate compartment of a sealed but openable container for the dentifrice and upon exerting pressure on the opened container the two dentifrice components are simultaneously admixed and extruded.

9. A dentifrice according to claim 8 wherein the dentifrice container has disposed therewithin two separate but connectable dentifrice spaces or compartments, each of which contains one component of the dentifrice and wherein the components are out of contact with one another prior to extrusion from the container ready for use.

10. A dentifrice according to claim 8 wherein the two dentifrice components are out of contact with one another prior to extrusion from the container by aerosolization.

11. An antimicrobial antiplaque dentifrice according to claim 1 wherein the PVP-I and peroxide components have the following percentage compositions:

|  | PVP-I Component | Peroxide Component |
| --- | --- | --- |
| Water | 26.64 | 31.39 |
| PVP-I (calculated as powder, 10% $I_2$) | 6.66 | — |
| Carbamide Peroxide | — | 1.86 |
| Sodium carboxymethylcellulose | 1.25 | 1.25 |
| Sorbitol | 23.75 | 23.75 |
| Dicalcium phosphate dihydrate | 40.2 | 40.2 |
| Sodium lauryl sulfate | 1.5 | 1.5 |
| Flavor, sweetener | q.s. | q.s. |

12. An antimicrobial antiplaque dentifrice according to claim 1 wherein the PVP-I and peroxide components have the following percentage compositions:

|  | PVP-I Component | Peroxide Component |
| --- | --- | --- |
| PVP-I (calculated as powder, | 10.0 | — |
| Carbamide Peroxide | — | 8.3 |
| Calcium carbonate | 34.0 | 40.0 |
| Sorbitol | 23.8 | 18.7 |
| Sodium lauryl sulfate | 1.5 | 1.5 |
| CMC (12 HP) | 1.3 | 1.3 |
| Water | 29.4 | 30.2 |
| Flavor, sweetener | q.s. | q.s. |

13. An antimicrobial antiplaque dentifrice according to claim 1 wherein the PVP-I and peroxide components have the following percentage compositions:

|  | PVP-I Component | Peroxide Component |
| --- | --- | --- |
| PVP-I (calculated as powder, 10% $I_2$) | 10.00 | — |
| Carbamide Peroxide | — | 8.3 |
| Silica (e.g., Syloid 244) | 15.0 | 20.0 |
| Sorbitol | 20.0 | 20.0 |
| Sodium lauryl sulfate | 1.5 | 1.5 |
| CMC (12 HP) | 3.0 | 3.0 |
| Water | 50.5 | 47.2 |

-continued

|  | PVP-I Component | Peroxide Component |
|---|---|---|
| Flavor, sweetener | q.s. | q.s. |

14. An antimicrobial antiplaque dentifrice according to claim 1 wherein the PVP-I and peroxide components have the following percentage compositions:

|  | PVP-I Component | Peroxide Component |
|---|---|---|
| PVP-I (calculated as powder, 10% $I_2$) | 10.0 | — |
| Dicalcium phosphate dihydrate | 69.0 | 70.7 |
| Calcium carbonate | 20.0 | 20.0 |
| Sodium lauryl sulfate | 1.0 | 1.0 |
| Flavor, sweetener | q.s. | q.s. |
| Carbamide peroxide | — | 8.3 |

15. An antimicrobial antiplaque dentifrice according to claim 1 wherein the PVP-I and peroxide components have the following percentage compositions:

|  | PVP-I Component | Peroxide Component |
|---|---|---|
| PVP-I (calculated as powder, 10% $I_2$) | 10.0 | — |
| Aluminum magnesium silicate | 1.5 | 1.5 |
| Benzoyl peroxide | — | 16.1 |
| Sodium carboxymethylcellulose (med. visc.) | 0.5 | 0.5 |
| Water | 30.3 | 24.2 |
| Sodium saccharine | 0.2 | 0.2 |
| Sorbitol (70% solution) | 15.0 | 15.0 |
| Glycerin | 10.0 | 10.0 |
| Dicalcium phosphate dihydrate | 26.0 | 26.0 |
| Tricalcium phosphate | 5.0 | 5.0 |
| Sodium lauryl sulfate | 1.5 | 1.5 |
| Flavor | q.s. | q.s. |

16. An antimicrobial antiplaque dentifrice according to claim 1 wherein the PVP-I and peroxide components have the following percentage compositions:

|  | PVP-I Component | Peroxide Component |
|---|---|---|
| PVP-I (calculated as powder, 10% $I_2$) | 10.00 | — |
| Carbamide Peroxide | — | 8.3 |
| Sorbitol (70% solution) | 20.00 | 15.00 |
| Calcium pyrophosphate | 40.00 | 26.00 |
| Sodium monofluorophosphate | 0.76 | — |
| Glycerin | 5.00 | 1.50 |
| Sodium lauryl sulfate | 1.50 | 1.50 |
| Magnesium aluminum silicate | 0.40 | 1.50 |
| Sodium carboxymethylcellulose | 1.15 | 0.5 |
| Stannous gluconate (31% solution) | 10.00 | 37.2 |
| Water | 11.19 | 37.2 |
| Flavor | q.s. | q.s. |

* * * * *